(12) United States Patent
Ensign et al.

(10) Patent No.: US 8,100,947 B2
(45) Date of Patent: Jan. 24, 2012

(54) LOW PROFILE PEDICLE SCREW AND ROD ASSEMBLY

(75) Inventors: Michael D. Ensign, Salt Lake City, UT (US); David T. Hawkes, Pleasant Grove, UT (US)

(73) Assignee: K2M, Inc., Leesburg, VA (US)

(*) Notice: Subject to any disclaimer, the term of this patent is extended or adjusted under 35 U.S.C. 154(b) by 729 days.

(21) Appl. No.: 11/440,549

(22) Filed: May 25, 2006

(65) Prior Publication Data

US 2006/0276792 A1 Dec. 7, 2006

Related U.S. Application Data

(60) Provisional application No. 60/684,695, filed on May 25, 2005.

(51) Int. Cl.
*A61B 17/70* (2006.01)
(52) U.S. Cl. .................... 606/267; 606/305
(58) Field of Classification Search .............. 606/59, 606/60, 277, 246–275, 300–320
See application file for complete search history.

(56) References Cited

U.S. PATENT DOCUMENTS

| | | | |
|---|---|---|---|
| 5,683,392 A * | 11/1997 | Richelsoph et al. | 606/272 |
| 5,817,094 A | 10/1998 | Errico et al. | |
| 5,882,350 A * | 3/1999 | Ralph et al. | 606/278 |
| 5,989,250 A | 11/1999 | Wagner et al. | |
| 6,273,888 B1 * | 8/2001 | Justis | 606/272 |
| 6,355,040 B1 | 3/2002 | Richelsoph et al. | |
| RE37,665 E | 4/2002 | Ralph et al. | |
| 6,402,752 B2 | 6/2002 | Schaffler-Wachter et al. | |
| 6,416,515 B1 * | 7/2002 | Wagner | 606/250 |
| 6,440,137 B1 | 8/2002 | Horvath et al. | |
| 6,740,086 B2 * | 5/2004 | Richelsoph | 606/60 |
| 7,090,674 B2 * | 8/2006 | Doubler et al. | 606/277 |
| 2002/0143341 A1 * | 10/2002 | Biedermann et al. | 606/73 |
| 2003/0167058 A1 * | 9/2003 | Shluzas | 606/61 |
| 2004/0176766 A1 * | 9/2004 | Shluzas | 606/65 |
| 2005/0096653 A1 * | 5/2005 | Doubler et al. | 606/61 |
| 2005/0137594 A1 * | 6/2005 | Doubler et al. | 606/61 |
| 2005/0154391 A1 * | 7/2005 | Doherty et al. | 606/61 |
| 2005/0261687 A1 * | 11/2005 | Garamszegi et al. | 606/61 |
| 2006/0004357 A1 * | 1/2006 | Lee et al. | 606/61 |
| 2006/0025768 A1 * | 2/2006 | Iott et al. | 606/61 |
| 2006/0074418 A1 * | 4/2006 | Jackson | 606/61 |
| 2006/0155278 A1 * | 7/2006 | Warnick | 606/61 |
| 2006/0200131 A1 * | 9/2006 | Chao et al. | 606/61 |
| 2006/0229615 A1 * | 10/2006 | Abdou | 606/61 |

* cited by examiner

*Primary Examiner* — Eduardo C Robert
*Assistant Examiner* — Lynnsy Schneider
(74) *Attorney, Agent, or Firm* — Carter, DeLuca, Farrell & Schmidt, LLP

(57) ABSTRACT

A pedicle screw and rod assembly is provided which has a low profile in the final assembled position. The pedicle screw includes a screw having a threaded portion and a head portion. A tulip is positioned on the head portion of the screw. A fastener assembly is coupled to the tulip and positioned to retain the tulip on the head portion. A rod retainer member is positioned inside the tulip and grips the rod, to hold it in position relative to the tulip assembly and pedicle screw. The top of rod retaining member is approximately equal in height to, or lower than the rod itself. This provides a low profile pedicle screw and rod assembly since the rod itself will normally be the uppermost member of the completed assembly.

8 Claims, 13 Drawing Sheets

LOW PROFILE PEDICLE SCREW AND ROD ASSEMBLY

RELATED APPLICATIONS

This application claims the benefit under 35 U.S.C. §119 (e) of U.S. Provisional Patent Application No. 60/684,695 filed May 25, 2005, titled "Low Profile Pedicle Screw and Rod Assembly." The provisional application is incorporated herein by reference in its entirety.

TECHNICAL FIELD

The present exemplary system and method relates to medical devices. More particularly, the present exemplary system and method relates to percutaneous pedicle screw and rod combinations that have a low profile in the final assembly.

BACKGROUND

One current technique for treatment of certain kinds of back injuries is to attach one or more rigid rods to a person's vertebra using screws which have been coupled to the one or more vertebra by threading into the bone. A tulip is coupled to a head of the screw. The rod is connected to the tulip and is secured in position on the tulip by one or more different types of fasteners.

Tulips currently available in the art are relatively large and obtrusive. For example, the tulip disclosed in U.S. Pat. No. 5,882,350 shows a large clamp member (24) coupled to a tulip (22), as shown in FIG. 1. A collet (14) may have one or more slots (18) to hold the tulip (22) on the head (12) of the screw (16). Another example of a rod and pedicle screw assembly is shown in U.S. Pat. No. 6,402,752, of which two figures are shown in FIGS. 2 and 3, respectively. These three figures show a rod (20) coupled to the head (12) of the screw (16). The tulip (22) has a top region (24) which aids in connecting the rod (20) to the head (12) of the screw (16). One or more side plates (26, 28) together with additional members (30, 32) assist in rigidly connecting the rod (20) to the screw (16). As can be seen in FIGS. 2 and 3, the tulip (22) extends a substantial distance above the head (12) of the screw (16). This results in a larger and more obtrusive pedicle screw assembly which increases both the tissue damage during surgery and recovery time needed after surgery.

Additionally, these and other conventional pedicle screw systems that are rather large and bulky may result in more tissue damage in and around the surgical site when the pedicle screw system is installed during surgery. The prior art pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

SUMMARY

In one of many possible embodiments, a pedicle screw and rod assembly is provided which has a low profile in the final assembled position. The pedicle screw includes a screw having a threaded portion and a head portion. A tulip is positioned on the head portion of the screw. A fastener assembly is coupled to the tulip and positioned to retain the tulip on the head portion. A rod retainer member is positioned inside the tulip and grips the rod, to hold it in position relative to the tulip assembly and pedicle screw. The top of rod retaining member is approximately equal to, or lower than the rod itself. This provides a low profile pedicle screw and rod assembly since the rod itself will normally be the uppermost member of the completed assembly.

Another exemplary embodiment provides a gripping region of the rod retaining member at an upper portion of the rod retaining member. The rod is placed into the rod retaining member and then the rod retaining member is depressed into the tulip. Pressure is exerted on the outer walls of the rod retaining member to compress the rod retaining member against the rod itself to grip the rod in a fixed position. Since the rod retaining member is pressed into the tulip itself, the uppermost portion of the rod retaining member is approximately equal to or less than the height of the topmost portion of the rod when in the final assembled position. Accordingly, the pedicle screw and rod assembly combination has a low profile, as would be permitted for a given rod.

Another embodiment of the present exemplary system and method provides a fastening member positioned inside the tulip to fasten the tulip to the head of the screw. According to a further alternative embodiment, the fastener member also includes a tab which engages the rod retaining member. The fastener tab is removably coupled to the rod retaining member so that the rod retaining member and fastener are securely positioned inside the tulip while it is inserted on the head of the screw. After they have been positioned on the head of the screw, the fastener is depressed onto the head of the screw, thus affixing the tulip to the head of the screw. In a later step, a tab on the fastener is depressed which releases the rod retaining member from the fastener to permit the rod retaining member to be depressed into the tulip which compresses the rod retaining member and applies a gripping force on the rod.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Figure 1:
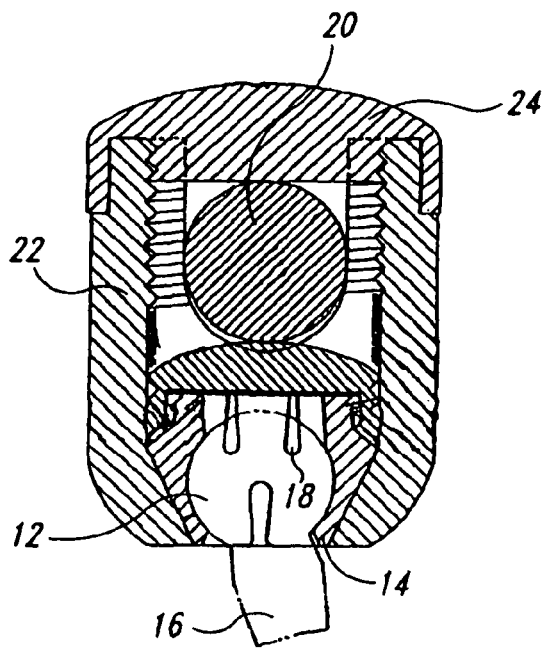
FIG. 1 is a cross sectional view of a pedicle screw and rod assembly as found in the prior art.
Figure 2:
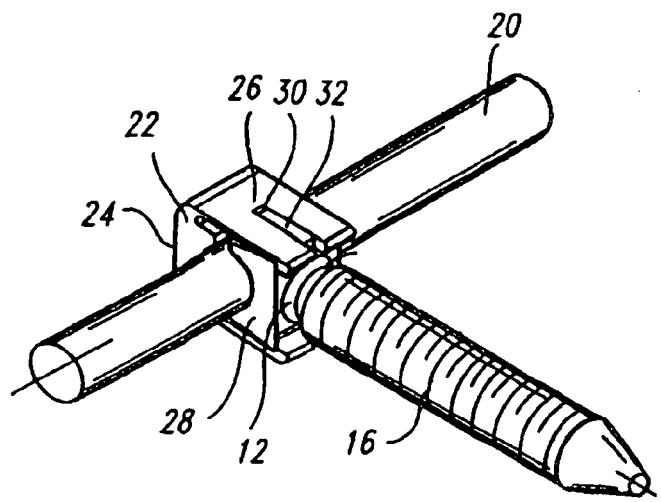
FIG. 2 is an isometric view of a rod coupled to a pedicle screw and tulip assembly according to the prior art.
Figure 3:
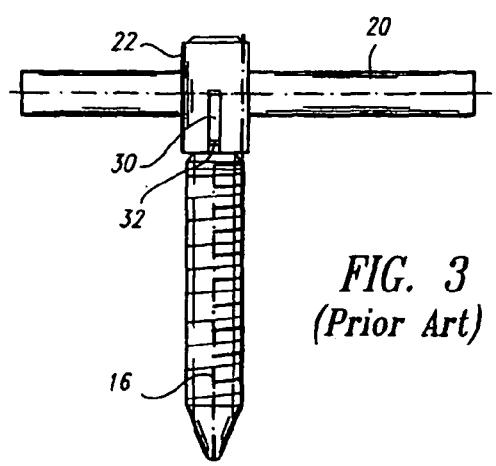
FIG. 3 is a side elevation view of the pedicle screw and rod assembly of FIG. 2 according to the prior art.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification provides a number of exemplary connection members and methods that can be used for any number of orthopedic rod placement systems. According to the present exemplary system and method, a pedicle screw and rod assembly is provided that has a low profile when in a final assembled position. Specifically, the present exemplary systems and methods provide for a pedicle screw and rod assembly system including a rod retaining member that is approximately equal to, or lower than the rod itself. This provides a low profile pedicle screw and rod assembly since the rod itself will normally be the uppermost member of the completed assembly. Further details of the present system and method will be provided in detail below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques with minimal tissue damage is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

In the following description, certain specific details are set forth in order to provide a thorough understanding of various embodiments of the present percutaneous pedicle screw system. However, one skilled in the relevant art will recognize that the present exemplary system and method may be practiced without one or more of these specific details, or with other methods, components, materials, etc. In other instances, well-known structures associated with pedicle screws have not been shown or described in detail to avoid unnecessarily obscuring descriptions of the embodiments of the systems and methods.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Figure 4:
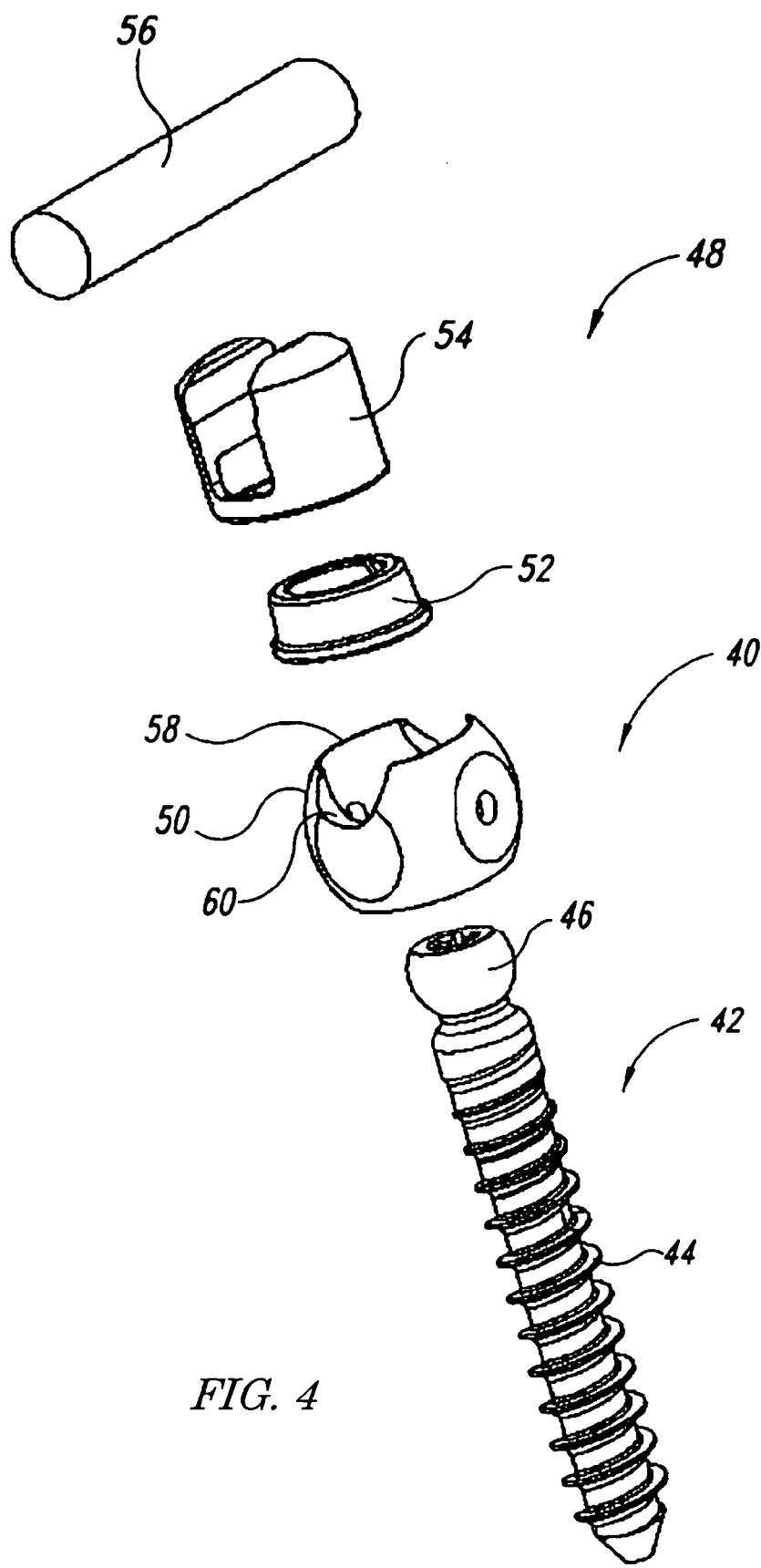
FIG. 4 is an exploded view of a pedicle screw tulip and rod assembly, according to one exemplary embodiment.

FIGS. 4-12 illustrate the present exemplary low profile pedicle screw and tulip assembly (40) according to a first exemplary embodiment. As shown in FIG. 4, the present exemplary low profile pedicle screw and tulip assembly (40) includes a pedicle screw (42) having a threaded portion (44) and a head portion (46), and a tulip assembly (48). The threaded portion (44) of the exemplary pedicle screw (42) is configured to be affixed to the bone of a patient during spine surgery. Particularly, as shown, the thread portion (44) of the exemplary pedicle screw (42) may include a self-tapping leading edge. According to this exemplary embodiment, the incorporation of a self-tapping leading edge in the thread portion (44) of the exemplary pedicle screw (42) provides the pedicle bone screw with the ability to remove bone material as it is being inserted, eliminating a step of a surgeon drilling a pilot hole prior to insertion of the bone screw. The head portion (46) of the pedicle bone screw (42) includes a number of functional features including, but in no way limited to, a plurality of driving features formed on a head base. According to one exemplary embodiment, at least the upper portion of the driving features may be engaged by a corresponding driving feature during installation. According to this exemplary embodiment, the corresponding driving feature (not shown) may engage the driving features and impart a rotational force thereon, driving the thread portion (44) of the pedicle bone screw (42) into a desired bone.

Additionally, as illustrated in FIG. 4, the tulip assembly (48) of the present exemplary low profile pedicle screw and tulip assembly (40) includes a tulip body (50) having a fastener (52) and a rod retaining member (54). Further, a rod (56) is positioned to be placed in the rod retaining member (54). According to the exemplary embodiment illustrated in FIG. 4, the tulip body (50) has an upper region (58) which includes a depression (60) in which the rod (56) is positioned in the final assembly.

According to the present exemplary embodiment, the fastener portion (52) of the tulip assembly (48) is positioned inside the tulip body (50). According to one exemplary embodiment, the fastener member (52) may include a split ring or an otherwise compressible ring member. When assembled, the fastener member (52) can be disposed within the internal portion of the tulip, or alternatively, the fastener assembly may be external to the tulip. Similarly, the rod retaining member (54) may be in the form of an outer portion of the tulip, a saddle, or some other member capable of gripping the rod (56) while also being retained by and held within the tulip body (50). Further details of the structure and operation of the present exemplary low profile pedicle screw and tulip assembly (40) will be provided below with reference to the figures.

Exemplary Method

According to principles of the present exemplary system and method, during insertion, the screw (42) is first placed in the appropriate position in the spine of a patient, such as in a vertebra in a manner well known in the art. Any additional preparation or work is may then be performed in order to ensure that the screw (42) is firmly implanted in the proper location in the patient for the particular surgery being performed.

Figure 5:
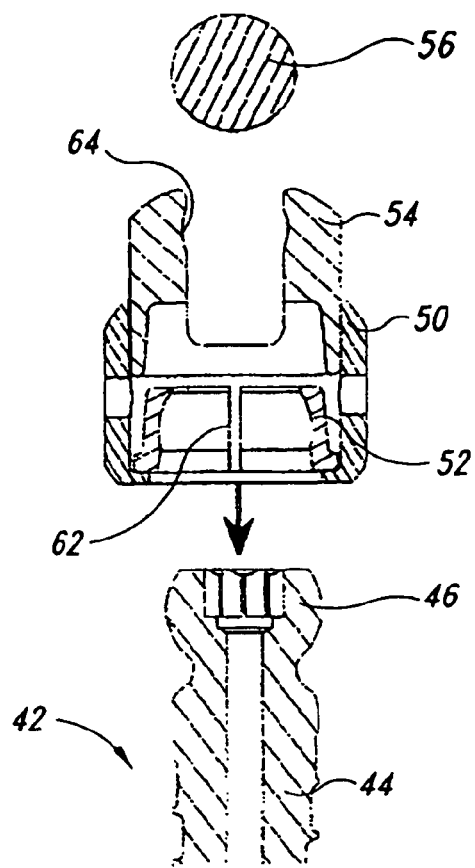
FIG. 5 is a cross sectional view of the pedicle screw, tulip and rod assembly of FIG. 4, according to one exemplary embodiment.
Figure 6:
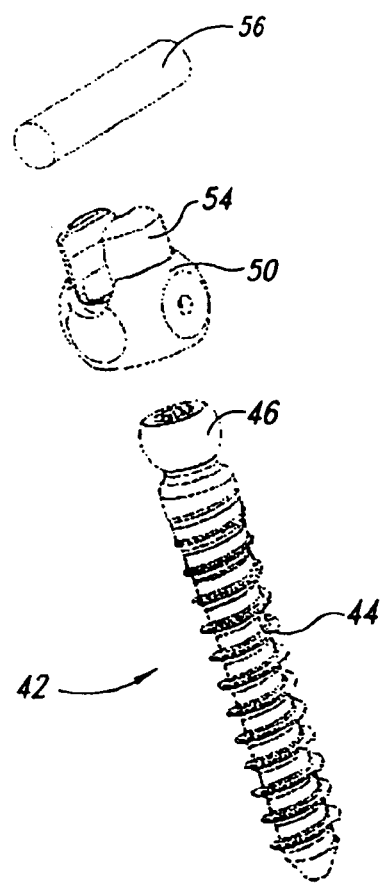
FIG. 6 is an isometric view of the pedicle screw, tulip and rod assembly in the position shown for FIG. 5, according to one exemplary embodiment.

FIGS. 5 and 6 illustrate the pedicle screw (42) in position for final assembly according to a first embodiment of the present exemplary system and method. As shown in the exemplary embodiment illustrated in FIGS. 5 and 6, the tulip body (50) includes the fastener member (52) positioned on an interior surface thereof. As mentioned, the fastener member (52) may include a slit (62), as shown, such that the fastener member operates as a compression ring and can be compressed from a first larger diameter to a smaller diameter. Additionally, the exemplary embodiment illustrated in FIGS. 5 and 6 includes the rod retaining member (54) positioned partially inside the tulip body (50), having a part adjacent an interior wall. As shown in FIGS. 5 and 6, the tulip assembly is partially assembled with the tulip body (50), the fastener member (52), and the rod retaining member (54) assembled together prior to being placed on the pedicle screw head (46). Alternatively, the above-mentioned components may be independently assembled onto the head (46) portion of the pedicle bone screw (42) one at a time.

Figure 7:
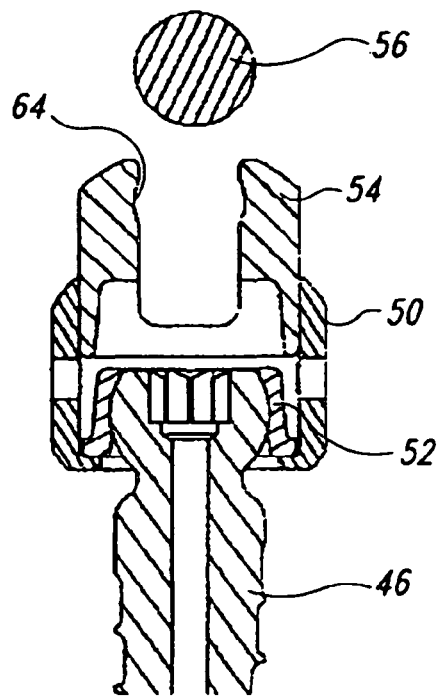
FIG. 7 is a cross sectional view of the pedicle screw and rod assembly of FIG. 5 in a further assembled position, according to one exemplary embodiment.
Figure 8:
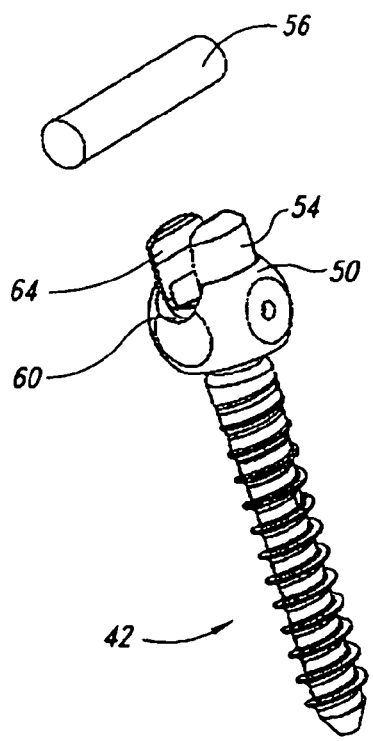
FIG. 8 is an isometric view of the assembly of FIG. 7, according to one exemplary embodiment.

FIGS. 7 and 8 illustrate the pedicle screw (42) and the tulip assembly (48) in the next stage of installation. As shown in FIGS. 7 and 8, the tulip assembly (48) is coupled to the head portion (46) of the pedicle screw (42). Specifically, when the fastener (52) is coupled to the head portion (46) of the pedicle screw (42), the fastener is expanded and imparts a compressive force on the head portion (46) of the pedicle screw (42). Consequently, the tulip assembly (48) is secured by a first compression fit to the pedicle screw.

In particular, the fastener (52), in the form of a compression ring in one exemplary embodiment, is forced over the head (46) of the pedicle screw, causing the fastener (52) to expand, slightly increasing the diameter of the fastener as permitted by the expansion slit (62). Once the fastener (52) has a portion thereof which goes beyond the largest diameter of the head (46) of the pedicle screw (42), the fastener compresses about the slit (62), reducing the diameter of the fastener, thereby connecting the tulip assembly to the pedicle screw. According to this exemplary embodiment, the fastener (52), in the form of a compression ring has a reduced diameter that is smaller than that needed in order to secure the head (46) onto the head.

As shown in FIGS. 7 and 8, when the fastener (52) is coupled to the head (46) of the pedicle screw (42), the rod retaining member (54) remains positioned against an upper inner wall of the tulip body (50). Alternatively, the rod retaining member (54) may be inserted into the tulip body (50) at this time if not pre-assembled. According to one exemplary embodiment, the rod retaining member (54) may be in the form of an inner tulip member and may also have a mating outer surface with the inner surface of the tulip body (50). The exemplary rod retaining member (54) illustrated in FIGS. 7 and 8 is cylindrical, which allows the rod retaining member to move freely within the tulip body (50) in a free state. Consequently, the rod retaining member (54) may therefore be rotated or tilted at various angles as deemed necessary for the particular patient and for proper connecting to the rod (56) to at an angle determined by the determined by the physician during the surgical procedure. Further, the fastener (52) may also be rotated or tilted, as appropriate.

Figure 9:
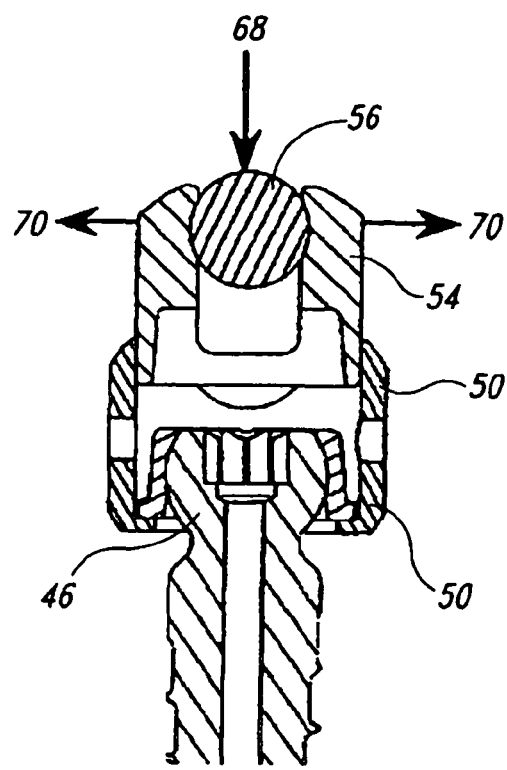
FIG. 9 is a cross sectional view of the rod being coupled to the tulip assembly of FIG. 4, according to one exemplary embodiment.
Figure 10:
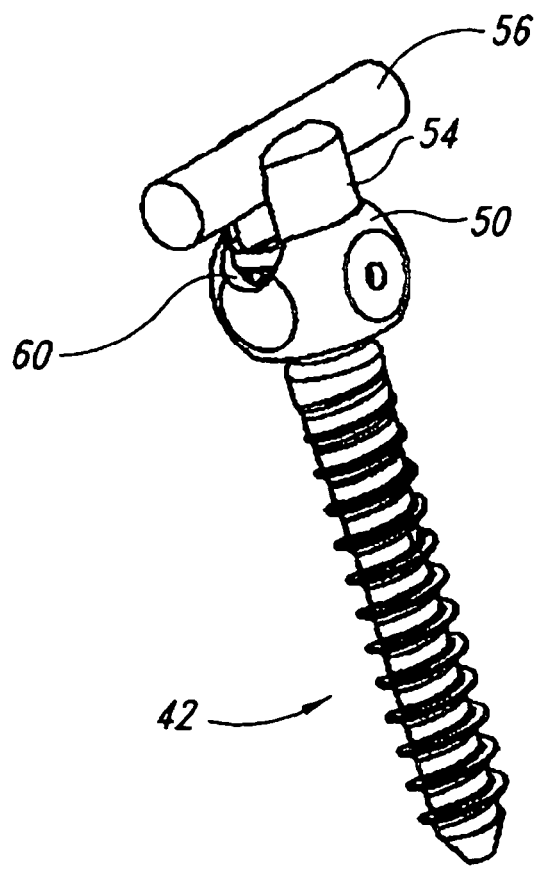
FIG. 10 is an isometric view of FIG. 9, according to one exemplary embodiment.

FIGS. 9 and 10 further illustrate the tulip assembly (49) in a next step of assembly. As shown in FIG. 9, the rod (56) is inserted into the gripping surface (64) of the rod retaining member (54) as shown. When inserted, an outward force is applied in the direction of the illustrated arrows (68). According to one exemplary embodiment, the rod (56) has a diameter which is slightly larger than the receiving diameter of the gripping members (64). The gripping members (64) are slightly resilient and will expand slightly in order for the rod (56) to be properly placed within the gripping member. As a result of the downward force (68) being applied on the rod (56), the rod retaining member (54) flexes slightly outward in the direction of the arrows (70). As the rod (56) passes the initial portion of the rod retaining member (54) and is seated within the gripping surface (64), the rod retaining member returns substantially back into position. While the rod retaining member (54) does substantially return with the rod (56) disposed in the gripping surface (64), the rod retaining member still exerts a compressive force on the rod (56) to retain it within the rod retaining member while in the raised position as shown in FIG. 9. The walls of the rod retaining member 54 are displaced laterally due to the mismatch in diameter between the rod (56) and the inner gripping member (64).

Figure 11:
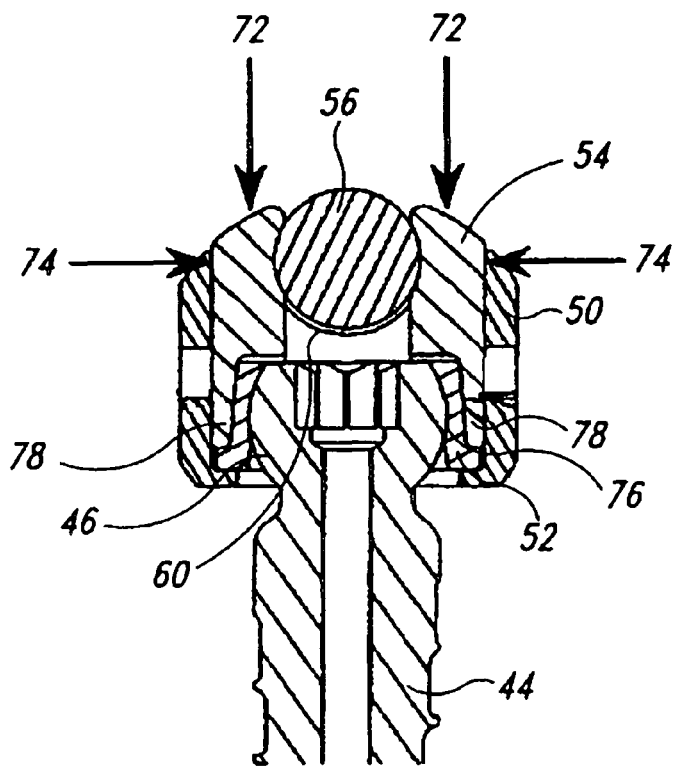
FIG. 11 is a cross sectional view of the final assembled pedicle screw, tulip and rod assembly of FIG. 4, according to one exemplary embodiment.
Figure 12:
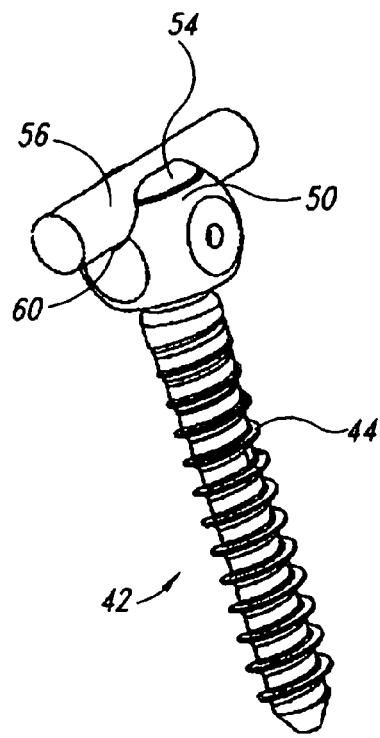
FIG. 12 is an isometric view of the final assembly of FIG. 11, according to one exemplary embodiment.

FIGS. 11 and 12 illustrate a fully engaged low profile pedicle screw and tulip assembly (40) according to one exemplary embodiment. As illustrated, the rod (56) is rigidly coupled to the rod retaining member (54) by applying a force (72) on the retaining member (54), pushing the rod (56) down into the tulip body (50). According to on exemplary embodiment, the downward force (72) is applied by imparting pressure to the rod retaining member (54) at the position shown by arrows 72. In some alternative embodiments, some pressure may also be applied to the rod (56) itself. As the rod retaining member (54) is pressed down into the tulip body (50), compression force (74) is applied to the rod retaining member (54) to more solidly press against the rod (56) and greatly increase the gripping force with which the rod (56) is held. Particularly, the inner surface of the tulip body (50) includes a compression feature or a shape configured to apply pressure to the outer portions of the rod retaining member (54). This may be achieved for example by having a taper in the inner surface of the tulip (50) so that pressure is applied against the rod retaining member (54) as it is depressed into the tulip. Alternatively, the rod retaining member (54) may include a slightly increasing taper in its outer diameter so that as the rod retaining member is pressed into the straight wall of the inner portion of the tulip body (50) additional pressure is applied to retain the rod (56). Additional alternative shapes may also be provided by which increased gripping pressure on the rod (56) is provided as the rod retaining member is pressed into the tulip body (50), as shown at arrows 74.

As the rod (56) and rod retaining member (54) are pressed down into the tulip body (50), the legs (78) of the rod retaining member (54) are compressed, further increasing the compression on the head (46) of the screw (42). Opposing tapers (76) may be formed on the fastener (52) to cause the compression ring to lock with a greater force on the head (46) of the pedicle screw (42) when in the position illustrated in FIG. 11. Having a taper (76) on the fastener (52) which mates with an extending leg (78) of the rod retaining member (54) provides a number of distinct advantages. Particularly, the shapes of the taper (76) and the legs (78) are selected so that a compression force (80) is applied inward, onto the fastener (52). The inward compression force (80) is achieved by having the legs (78) slightly increase in diameter as they go upward, causing greater force to be applied as the rod retaining member (54) is pressed down onto the fastener (52). Additionally, an inward compression force (80) is also achieved by having a slight outward taper in the fastener itself (52). Other methods may also be incorporated including, but in no way limited to, an increased diameter in one or both of the members or some other interlocking shape. As the rod retaining member (54) and fastener (52) are forced together, the fastener (52) is compressed and locked within the tulip body (50). Not only is additional force provided on the head (46) of the pedicle screw (42), but additional force is applied outward, on the tulip body (50), thus substantially increasing the retaining force of the rod on the tulip body. The final assembled rod tulip and pedicle screw assembly are shown in FIG. 12.

As illustrated in FIGS. 11 and 12 together, the topmost portion of the rod (56) is the highest member of the assembly. Particularly, the rod (56) is slightly higher than the sidewalls of the rod retaining member (54). In one embodiment, the relative sizes of the components are selected to ensure that the top portion of the rod (56) is always the highest member of the combined assembly, even if only slightly. In other embodiments, the top portion of the rod retaining member is approximately equal in height to the topmost portion of the rod (56). This particular embodiment is also shown in FIGS. 11 and 12 since the relative heights are approximately equal to each other. As illustrated, the rod (56) rests in a depression (60) of the tulip body (50) so that the entire assembly is less obtrusive and recessed, resulting in less tissue damage, and irritation to the patient and reduced healing times.

Alternative Embodiments

Figure 13:
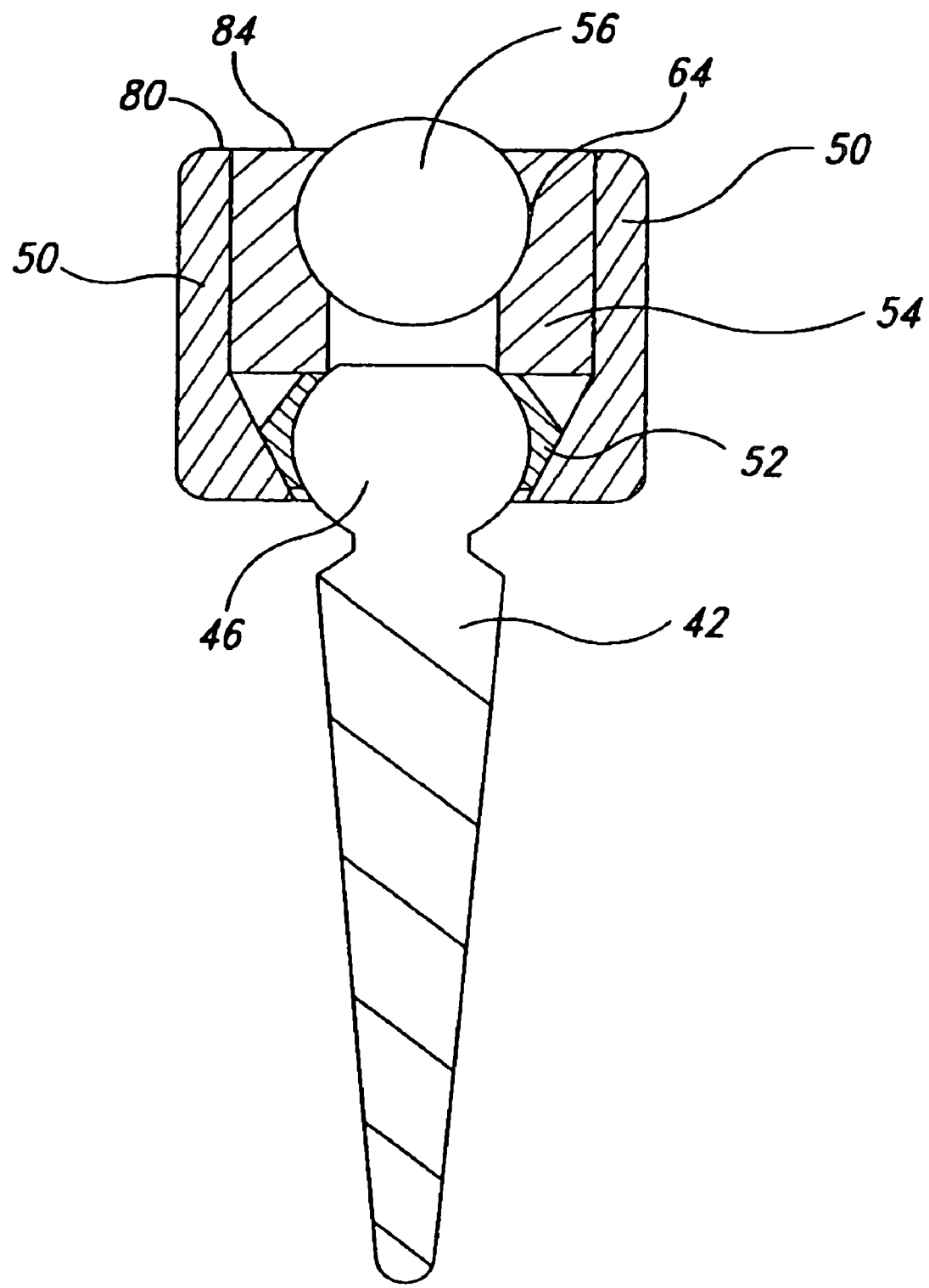
FIG. 13 shows a side elevation and partial cross sectional view of the pedicle screw and rod assembly according to a second exemplary embodiment.

FIG. 13 illustrates a cross-sectional view of a further alternative embodiment according to the present system and method. In the alternative embodiment of FIG. 13, the rod retaining member (54) is substantially more recessed than in the prior embodiment of FIGS. 4-12. As can be seen, the topmost surface (84) of the rod retaining member (54) is approximately flush with the topmost surface (80) of the tulip body (50). Consequently, the tulip body (50) is even with the highest portion of the combined tulip assembly such that no member protrudes higher than the tulip body itself that is a portion of the tulip assembly. The top surface (80) of the tulip body and surface (84) of the rod retaining member are flush with each other. As shown, the rod (56) is positioned within the rod retaining member (54) and held between gripping surfaces (62).

A fastener (52) in the form of a collet, a split ring, or other acceptable fastener for affixing to the head (46) of the pedicle screw (42) is also provided. The appropriate tapers and shapes are provided to impart the compression forces to rigidly hold the tulip body on the head (46) of the pedicle screw (42) in a manner similar to that shown for the other embodiments. A mating relationship between the rod retaining member (54), the inner surface of tulip body (50) and the fastener (52) is also provided so that when finally assembled a strong compression on both the head (46) of the pedicle screw and the rod (56) is assured.

Figure 14:
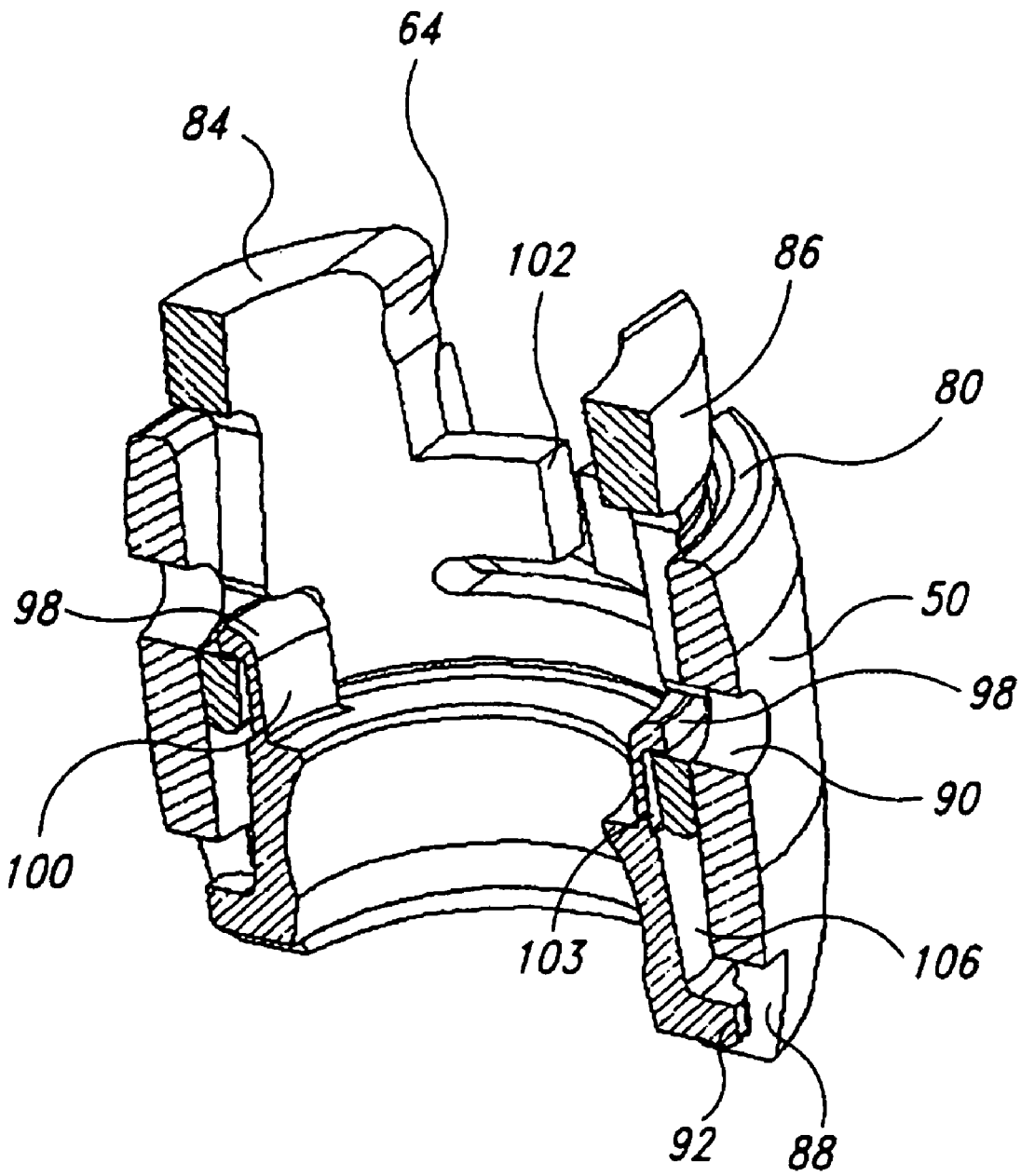
FIG. 14 shows a cross sectional isometric view of a tulip assembly according to a third exemplary embodiment.
Figure 15:
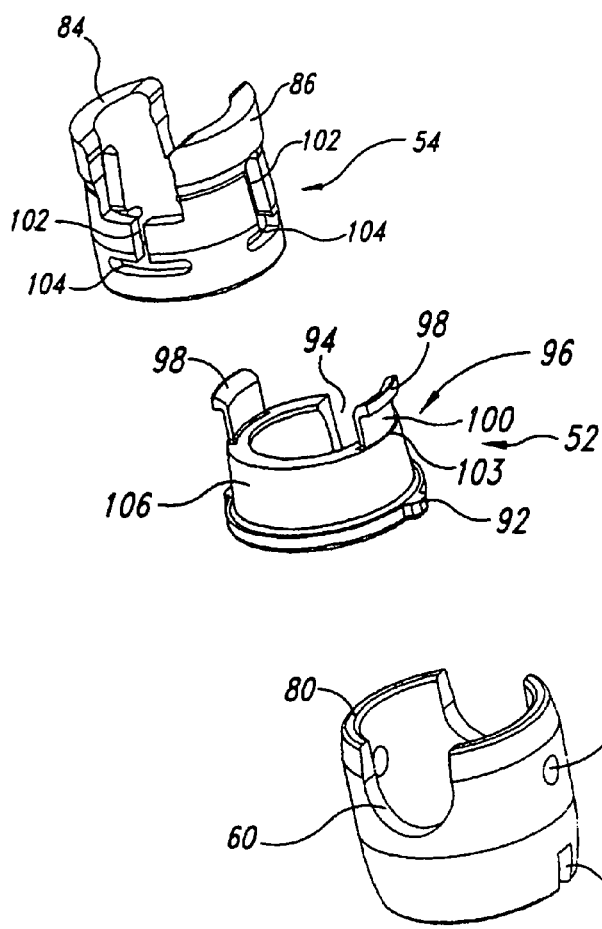
FIG. 15 shows an exploded view of the exemplary embodiment of FIG. 14.

In addition to the alternative embodiment illustrated in FIG. 13, FIGS. 14-19 illustrate a further alternative embodiment of a tulip assembly with a low profile pedicle screw and rod assembly according to one exemplary embodiment. As shown in FIGS. 14 and 15, the exemplary alternative embodiment includes a tulip body (50) and a rod retaining member (54).

Referring jointly to FIGS. 14 and 15, a tulip body (50) is shown having a fastener (52) sized to be positioned on an interior surface thereof and a rod retaining member (54) also sized to be positioned on an interior surface thereof. According to the illustrated exemplary embodiment, the tulip body (50) includes a recessed region (60) which is shaped and positioned to receive a rod (56) as explained herein below. A first aperture (88) at a bottom portion of the tulip body (50) is positioned to receive a base tab (92) of a fastener and a second aperture (90) formed at a central portion of the tulip body (50) is positioned to receive a locking tool (110) as explained later herein.

An interior surface of the tulip body (50) is shaped to provide the appropriate compression forces on the interior components as the tulip body is assembled as explained later herein. Particularly, a fastener (52) is shaped to be positioned within the tulip body (50) as shown in FIGS. 14 and 15. The fastener (52) may be in the form of a split ring having a split (94) in one side thereof. According to one exemplary embodiment, the split may be a complete aperture that extends completely through the fastener (52) so the fastener (52) is a "C" shaped fastener with a small opening. Alternatively, the fastener (52) may be in the form of a collet, a compression ring, a partial split ring or other acceptable shape based on the purpose and function as explained herein.

In one exemplary embodiment, the fastener (52) includes a base tab (92) and an engaging tab (96). The engaging tab (96) includes a tab body (100) having a tab flange (98) at a top portion thereof and a shelf (103) at a bottom portion thereof.

The shelf (103) is present in one alternative embodiment, but is not present in other alternative embodiments. The fastener (52) has a body portion (106) which is tapered and sized to fit within the interior surface of the tulip body (50) as shown in FIG. 14, according to one exemplary embodiment.

The rod retaining member (54) is also preferably in the shape of a ring that mates with the interior surface of the tulip body (50) and also engages the fastener (52). According to one exemplary configuration, the rod retaining member (54) includes one or more vertical slits (102) which are configured to permit the diameter of the retaining member (54) to increase or decrease depending on applied forces. Additionally, according to one exemplary embodiment, the rod retaining member (54) may also include one or more horizontal slits (104) which assist in permitting additional compressions and expansion in the vertical direction while the slits (102) provide compression in the annular or horizontal direction.

The rod retaining member (54) may also include, according to one exemplary embodiment, an upper flange having a rod gripping surface (64) on an inner surface thereof and a shoulder portion (86). According to this exemplary embodiment, the rod retaining member (54) engages the fastener (52) as shown in FIG. 14 when placed inside the tulip body (50).

In particular, the engaging tab (96) has an upper shoulder portion (98) which enters the horizontal slot (104) to couple the fastener (52) to the rod retaining member (54). The exemplary fastener (52) includes base tabs (92) which are positioned within the aperture (88) of the tulip body (50). This particular assembly of the rod retaining member (54) and the fastener (52) inside the tulip body (50) has some tolerance to permit free play of a slight amount between the components. The amount of play permitted between the various components can be designed according to a preferred configuration. The base tabs (92), according to one exemplary embodiment, fit into slots (88) of the tulip body (50) to prevent the fastener (52) from exiting out of the top of the body. The fastener (52) can, however, be pressed downward without being stopped by interference between the tabs (92) and the tulip body (50).

Further, the rod retaining member (54) has a shoulder (86) which has a larger diameter than the inner diameter of the tulip body (50). The shoulder (86) prevents the rod retaining member (54) from being pushed downward, through the bottom of the tulip body (50) since it would engage an upper surface (80). On the other hand, however, the shoulder (86) does not prevent free movement upward.

When the two components, the fastener (52) and the rod retaining member (54), are placed together inside the tulip body (50), the engaging tab (96) having the flange (98) locks the two members together as shown in FIG. 14. Particularly, the flange (98) engages the slot (104) to hold the two members together. With the two members locked together, the fastener (52) prevents the assembly from being pressed out of the top of the tulip body (50) because of the tab (92) and the rod retaining member (54) prevents the combined assembly from falling out of the bottom of the tulip body by the shoulder (86). Accordingly, when engaged together with the engaging tab (96), the assembly is held together as a unitary member with all three components, the tulip body, the fastener and the rod retaining member interconnected with each other. The relative play between the components is determined by the relative positions of the tabs (92, 96) and the shoulder (86) and can be selectively set in a range between tight and loose, depending on the design parameters. The ability to modify one or more components to select the tightness of the connections inside the tulip body is a particular advantage of the present exemplary system and method.

As illustrated in FIG. 14, the entire tulip assembly is a single piece that a physician can hold in one hand and place onto the head (46) of a pedicle screw (42). In other words, there are no loose parts which may fall out or need to be assembled by the physician. Having the entire tulip assembly as a single piece, ready for use by the physician is a further substantial advantage of the present system and method. The only parts that are separate, according to one exemplary embodiment, are the screw (42) and the rod (56). These components can be easily assembled during the surgery, as described below. According to one exemplary embodiment, there is sufficient tolerance and play in the pre-assembled tulip assembly to permit a wide range of patients to use the same tulip assembly design.

Figure 16:
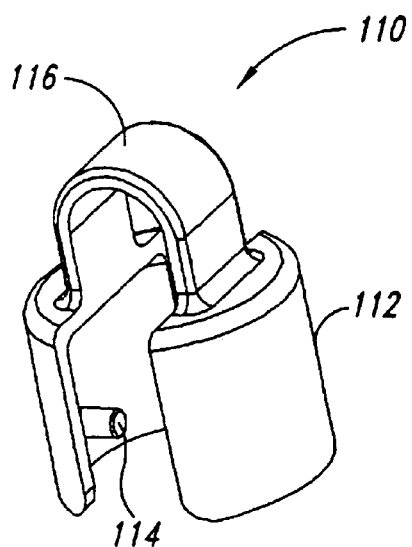
FIG. 16 shows a locking tool usable with the embodiment of FIG. 14 in order to lock the rod into the tulip and pedicle screw assembly, according to one exemplary embodiment.

FIG. 16 illustrates a locking tool (110) which is used to release the rod retaining member (54) and permit the rod retaining member (54) to be depressed to lock onto the head (46), according to one exemplary embodiment. As illustrated, the exemplary locking tool (110) includes a release pin (114) on an inner surface which is configured to press onto the engagement tab (96) of the fastener (52), as explained later herein. A handle (116) may also be formed on the locking tool (110) to permit the locking tool (110) to be more easily moved by a physician. Of course, FIG. 16 is just one exemplary embodiment of a locking tool configuration and the locking tool (110) may assume any number of different configurations. For example, according to one exemplary embodiment, the locking tool (110) may be configured as a simple bar with a pin (114) without the need for the outer housing (112) and the handle (116). Other configurations of the locking tool (110) are also acceptable as will be clear from the design parameters explained herein.

Figure 17A:
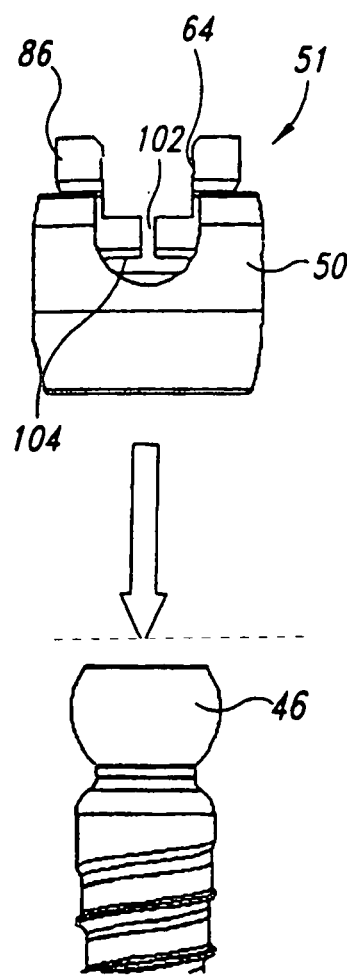
FIG. 17A shows the tulip of the exemplary embodiment of FIG. 14 prepared for positioning on a pedicle screw, according to one exemplary embodiment.
Figure 17B:
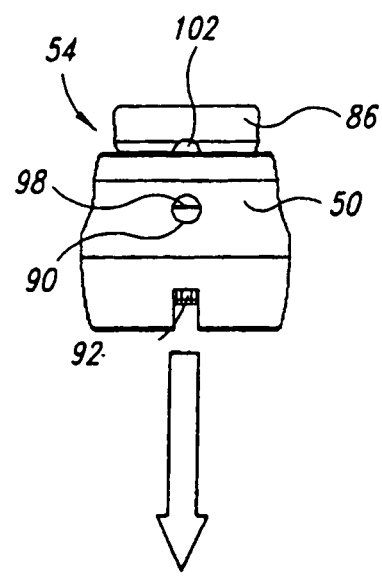
FIG. 17B is a side view of the exemplary embodiment of FIG. 17A.
Figure 17B:
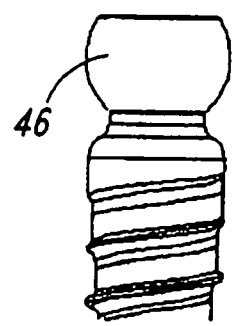

FIGS. 17A-23, described in detail below, illustrate the method of constructing the pedicle screw and rod assembly according to this exemplary embodiment. As shown in FIG. 17A, the tulip assembly is preassembled having the three components coupled to each other. The tulip body has the fastener (52) and the rod retaining member (54) loosely coupled to each other inside the interior surface of the tool body (50). As mentioned in previous embodiments, the pedicle screw (42) having the head (46) is affixed to the vertebra of the patient undergoing surgery. As can be seen in FIG. 15, the fastener (52) has one or more slits (94) therein which permit the fastener (52) to expand slightly to a larger internal diameter so that the fastener may fit around the top of the head (46). According to one exemplary embodiment the fastener (52) is somewhat resilient so that once it slides over the largest diameter portion of the head (46) it compresses over the base of the head (46). In many embodiments, the head (46) will be generally spherical, however other shapes may also be acceptable as there are many known in the art. As shown in the side view of FIG. 17B, the flange (98) is positioned adjacent the aperture (90) when the tulip assembly is assembled.

With the tulip assembly positioned on the head (46), movement of the tulip assembly is still possible. Consequently, the tulip assembly may be rotated around the head (46) to position in any desired angular orientation. In addition, the tulip assembly may be tilted in any direction, forwards, backwards or radially as desired. The fastener (52), when first coupled onto the head (46) forms a rotatable connection similar to that of a ball joint.

Figure 18A:
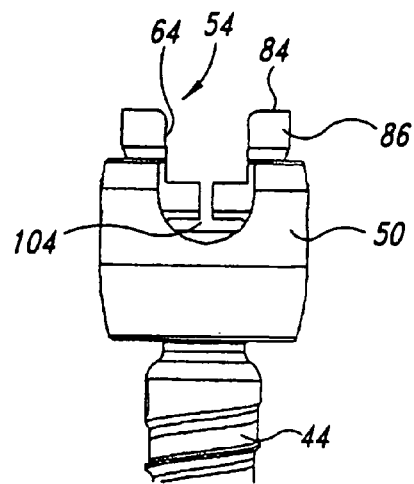
FIG. 18A illustrates the tulip assembly positioned on the pedicle screw of the exemplary embodiment of FIG. 14, according to one exemplary embodiment.
Figure 18B:
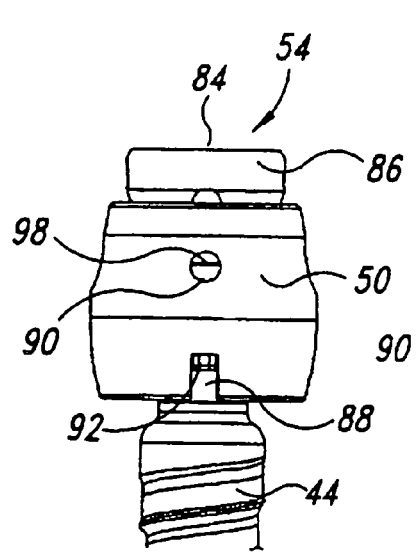
FIG. 18B is a side view of the exemplary embodiment in the position of FIG. 18A.

FIGS. 18A and 18B are two views of the present exemplary tulip assembly positioned on the head (46). FIG. 18A is a side view illustrating the gripping surface (64) through which the rod (56) will extend, according to one exemplary embodiment. FIG. 18B is a side view oriented approximately 90 degrees from that shown in FIG. 18A. FIG. 18B illustrates side view of the shoulder (86) and a view of the aperture (90) having the flange (98) of the engaging tab (96) visible through the aperture. As illustrated, the base tab (92) is in the high position in the aperture (88). In this exemplary position, the tulip assembly is locked onto the head (46) because the split ring fastener (52) is exerting a compression force around the tulip head (46). However the fit provided by the split ring fastener (52) is a sufficiently loose fit that the fastener may be rotated relative to the head (46).

As shown in FIGS. 18A and 18B, the shoulder (86) of the rod retaining member (54) extends completely above the tulip body (50). Consequently, there is little or no compressive force on the shoulders (86) of the rod retaining member (54) in this configuration so that they may easily receive the rod (56) to be inserted therein at a later step.

Figure 19:
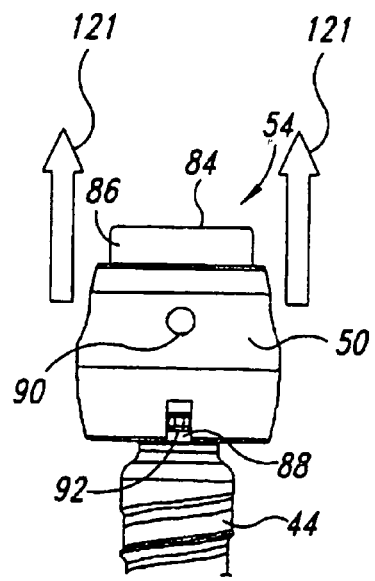
FIG. 19 shows the tulip assembly in position for performing a spondy reduction on the spine.

FIG. 19 illustrates the use of the present exemplary tulip assembly during one or more surgical procedures. For example, during some surgical procedures, it is desirable for the physician to perform a procedure known as a spondy reduction. A spondy reduction is carried out when the position of the individual vertebrae are not properly aligned within the spinal column of a person's back. For example, one vertebra may have moved anterior to the spine as a whole so that it is out of proper alignment. When a spondy reduction is to be carried out, some force is applied to the tulip body (50) in the direction of the arrows (121). The force (121) may be applied by a tool grasping the tulip body (50) or by the physician, with his or her fingers, grasping the tulip body (50) or some other instrument being used to move and align the pedicle screw and vertebra combination.

According to principles of the present exemplary system and method, one convenient way by which this can be done is if the physician grasps, either by hand or with an instrument, the tulip body (50) and pulls in the direction of the arrows (121) to apply force. When force is applied as illustrated, the tulip body (50) rises to move slightly away from the head (46). When the tulip body (50) rises, the tab (92) inside the aperture (88), however, does not move relative to the head (46). The fastener (52) of which the base tab (92) is a portion stays in its current position on the head (46). When the tulip body 50 is pulled up, the fastener (52) drops into the locked position with the base tabs (92) in the low position as shown in FIG. 19. This compresses on the screw head (46) to prevent disassembly during a spondy reduction procedure. In one exemplary embodiment, the relative sizes of the internal surface of the tulip body (50) and the outer surface of the fastener (52) may be selected to apply additional force against the fastener (52). For example, an upper portion of the fastener (52) may have an enlarged segment or a taper so that as the tulip body (50) is pulled up the enlarged segment or taper applies additional compressive force on the fastener (52) to more tightly clamp the fastener to the head (46). Alternatively, according to one exemplary embodiment, the tulip body interior surface may be tapered so as to apply additional force. Other arrangements may also be made as will be known in the art in order to ensure that the fastener (52) remains locked on the head (46) as the tulip body (50) is moved. As the force is applied in the spondy reduction, the shoulder (86) will slightly enter the tulip body (50) since the tulip body moves upward relative to the head of the screw while the fastener (52) and the rod retaining member (54) maintain the same relationship relative to each other and to the screw head (46). The force is then applied in the direction of the arrows (121), or other directions until the vertebrae are properly aligned.

Figure 20:
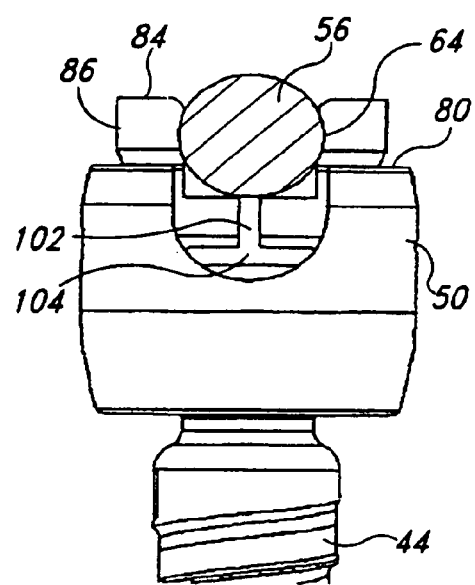
FIG. 20 shows the rod positioning the tulip assembly in preparation for final assembly.
Figure 21:
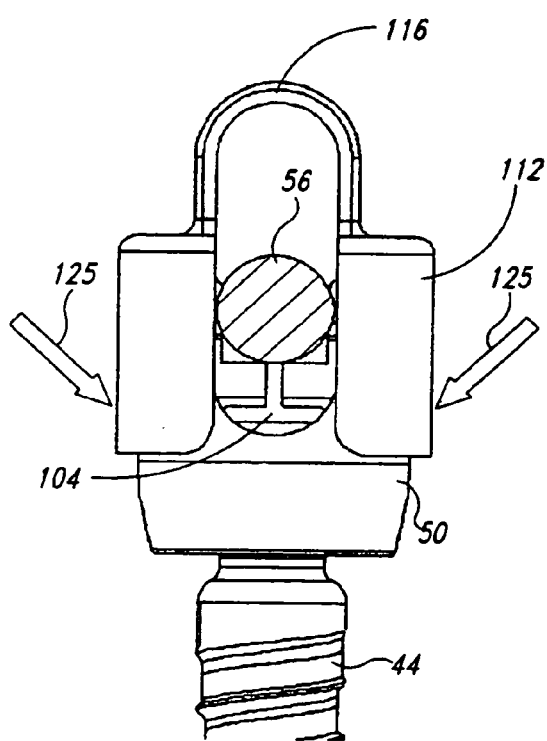
FIG. 21 shows a side elevation view of the locking tool in position to lock the rod onto the tulip.

FIGS. 20-23 illustrate the tulip assembly having a rod attached thereto, according to various positions. As shown in FIG. 20, a rod (56) is snapped into the shoulder portion (84) of the rod retaining member (54). The rod (56) is pressed down until it fits in the corresponding concave region of the gripping member (64). The gripping member (64) may, according to one exemplary embodiment, have the appropriate contoured or gripping surface in order to provide a high compression and high friction fit onto the rod (56). The slots (102) permit the shoulders (86) to flex slightly outward so that the rod retaining member (54) has a slightly larger diameter as the rod (56) is pressed down into them. When the rod (56) is in the gripping member (64), the shoulders (86) compress around the rod (56), thus reducing slightly in diameter but still being somewhat larger in diameter than when the rod (56) is not present. Therefore, the rod (56) is held with some compression force from the shoulders (86). In this position, the locking tool (110) is then placed over the combined tulip and rod assembly. The release pin (114) is positioned to enter the aperture (90) of the tulip body (50). Upon entering the aperture (90), the release pins extend through the apertures (90) to contact the flange (98) of the engagement tab (96). Usually, based on the position of the engagement tab (96), the release pins (114) will abut directly against the flange (98). When a force is applied in the direction of the arrows (125), the release pins (114) depress the engagement tab (96) on the fastener, thus releasing the rod retaining member (54).

In one exemplary embodiment, the rod retaining member (54) includes a bottom portion which engages with the shoulder (103) of the engagement tab (96). The shoulder (103) prevents the rod retaining member (54) from being pressed downward into the tulip body (50) when the rod is not present. Thus, the rod retaining member (54) stays in a high position ready to receive the rod. Once the engagement tabs (96) are depressed by the release pin (16), the rod retaining member (54) falls off the shoulder (103) and can be pressed deeper down into the interior of the tulip body (50). In some alternative embodiments, the shoulder (103) is not present and a separate release tool (110) is not necessary. Rather, in these alternative embodiments, the rod retaining member (54) has even greater play and is permitted to travel somewhat down into the tulip assembly and the tulip body (50), the restraining force being from the shoulder (98), preventing the rod retaining member from going further up out of the tulip body but not prohibiting it from descending into the tulip body. Other alternative arrangements are also possible in which the shoulders (86) are held in the upward position so that the rod (56) may be force-snapped into the retaining member while keeping the rod retaining member from being pressed down into the tulip body (50) until the physician is ready to make the final adjustments and connections.

Figure 22:
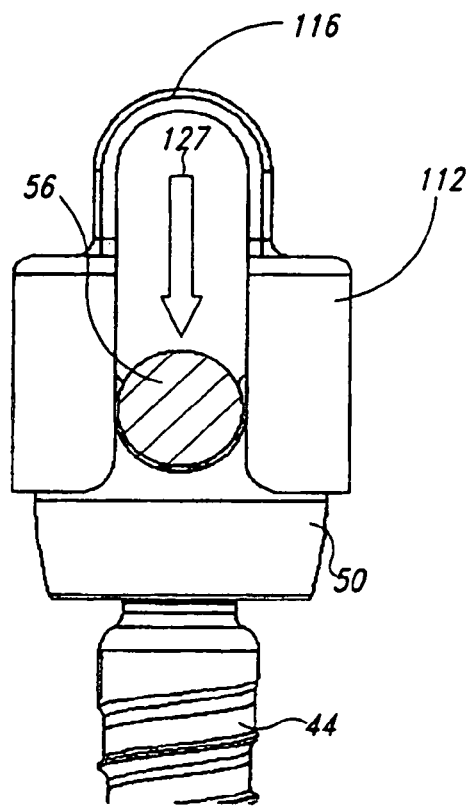
FIG. 22 shows a side elevation view of the rod being locked onto the tulip.

FIG. 22 illustrates a force (127) which is applied overall to the rod assembly (56) and the rod retaining member (54). This force (127) can be applied directly to the rod (56), to the rod retaining member (54), or to both together. When the force (127) is applied in the direction illustrated in FIG. 22, the rod retaining member (54) is depressed down into the tulip body (50). The shoulders (86) have a slightly larger diameter along the outer surface than the interior surface of the tulip body (50). As the shoulders (86) are pressed down into the tulip body, the shoulders are forced inward with a high compression force providing a very high retaining force on the rod (56). The relative shape between the rod retaining member (54) and the interior surface of the tulip body (50) is selected to provide the desired gripping force. The shoulders (86) may be tapered to gradually increase to a thick shoulder near the very top region so as to apply a very large gripping and retaining force onto an upper portion of the rod (56). The gripping force would thus increase the deeper the retaining member (54) is pressed into the tulip body (50). Alternatively, the shoulders (86) may have a uniform thickness so that an even gripping force is applied across the arcuate gripping surface (64) to the rod (56). As a further design feature the interior surface of the tulip body (50) may be slightly tapered so as to provide a greater application force against the rod retaining member (54) as it is pressed down into the tulip body.

In addition, the base region of the rod retaining member (54) may also be slightly tapered so that it engages the fastener (52) with a greater force. As can be seen in FIGS. 14 and 15, the fastener (52) can have a slightly enlarged taper near its base to have a slightly larger diameter. As the rod retaining member (54) is depressed into the tulip body (50), the larger diameter near the base applies an even greater force on the fastener (52), thereby more securely locking the fastener (52) onto the head (46). The force with which the fastener (52) is gripped onto the head (46) is selected to be sufficiently great that the tulip assembly is held in an immovable position rigidly grasping the rod in a desired fixed position as selected by the physician during the surgical procedure. Up until the time when the rod retaining member (54) is depressed, the physician has substantial freedom of movement of rotating the tulip assembly to various positions in order to be suited for the particular surgical need. Once the rod (56) is placed into the rod retaining member, the physician is permitted to make additional final adjustments in order to place the various spine members in the proper position as well as other components which may have been attached or inserted during the surgical procedure. When all of the components in the various spine members are the correct position then the physician depresses the rod retaining member (54) deeply into the tulip body (50) in order to solidly lock all portions of the tulip assembly relative to the pedicle screw head (46) and the rod (56). This provides a complete lock of all members relative to each other so that further movement does not occur. The fastener (52) grips the head (46) with a very tight grip in the position selected by the physician. In addition, the rod (56) is tightly held in position by the rod retaining member (54). The interior surface of the tulip body (50) is contoured in order to apply high compression forces to both via the fastener and the rod retaining member (54) to ensure that all members are retained in a fixed position. Of course, the amount of compression and the relative location of the compression can be selected according to desired design by selection of the shape and taper and relative contour of the interior of the tulip body or the exterior surfaces of the fastener (52) and the rod retaining member (54) relative to each other.

Figure 23:
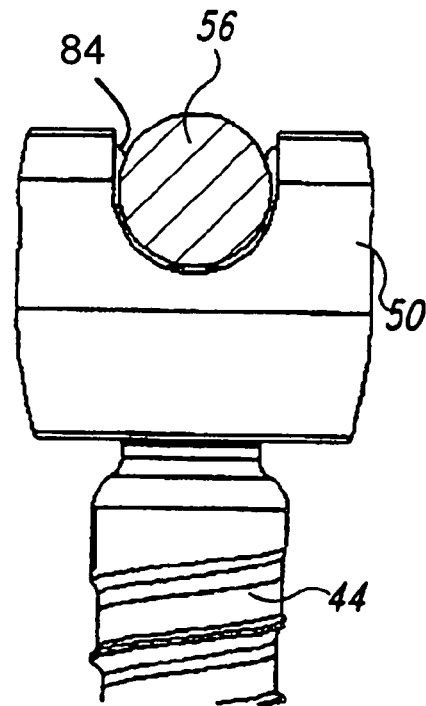
FIG. 23 shows a side elevation view in the final assembled position with the rod fixed to the pedicle screw via the tulip assembly.

FIG. 23 illustrates the completed pedicle screw, tulip and rod assembly. As can be seen in FIG. 23, the rod retaining member (54) is pressed downward until its top surface (84) is flush with or even slightly recessed below the top surface (80) of the tulip body (50). In the FIG. as shown, the top surface (84) of rod retaining member (54) is slightly depressed some amount below the uppermost surface (80) of the tulip body as can be seen in FIG. 23. This creates a slight recess which may be conveniently used by the physician for other medical purposes. The rod (56) is pressed down to be adjacent to or perhaps abut against the recess (60) in the tulip body (50). Preferably, according to one exemplary embodiment, the rod (56) is just slightly spaced above the recess (60) so that it is fully engaged by and in contact with only the rod retaining member (54). Alternatively, the physician may continue to depress the rod retaining member (54) until the rod (56) abuts against the depression (60), thus assuring the physician that the rod (56) has been sufficiently depressed that a guaranteed tight compression fit of the entire tulip assembly, pedicle screw and rod has been achieved. The size of the depression (60) is therefore selected in order to ensure that the proper compression forces are applied when the rod (56) has been sufficiently pressed into the depression (60).

As can be seen in FIG. 23, the uppermost portion of the rod (56) is approximately adjacent to the uppermost portion of the tulip body (50). In one embodiment, the uppermost portions are approximately equal to each other. In alternative embodiments, the uppermost portion of the tulip body may be slightly smaller so that the rod (56) is somewhat higher.

In conclusion, the present exemplary percutaneous pedicle screw systems and methods provide a number of exemplary connection members and methods that can be used for percutaneous screw placement. Specifically, the present exemplary systems and methods provide for a low profile pedicle screw and tulip assembly that limits the size of the tulip such that the tulip is even with or lower than the top of the rod when fully engaged. The resulting low profile of the present exemplary pedicle screw and tulip assembly results in less tissue damage and irritation in and around the surgical site, when compared to traditional systems.

All of the above U.S. patents, U.S. patent application publications, U.S. patent applications, foreign patents, foreign patent applications and non-patent publications referred to in this specification and/or listed in the Application Data sheet, are incorporated herein by reference, in their entirety.

It will be understood that various modifications may be made without departing from the spirit and scope of the present exemplary systems and methods. For example, while the exemplary implementations have been described and shown using screws to anchor into bony structures, the scope of the present exemplary system and methods is not so limited. Any means of anchoring can be used, such as a cam, screw, staple, nail, pin, or hook.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A pedicle screw and rod assembly for securing a rod, comprising:
   a screw having a threaded portion and a head portion; a tulip positioned on the head portion of the screw, the tulip being configured to couple the rod, the tulip including at least one side orifice providing access to an inner cavity of the tulip;
   a fastener assembly associated with the tulip, the fastener assembly being positioned adjacent the head portion of the screw in direct contact therewith to retain the tulip assembly on the screw;
   a rod retaining member coupled to the tulip, between the fastener assembly and the tulip the rod retaining member having a ripping region for holding the rod in a fixed position relative to the tulip, the gripping region defining at least in part a substantially circular shape, the gripping region being positioned such that a top most portion of the rod retaining member and the fastener assembly are defined by heights that are less than the height of the top most portion of the rod and the substantially circular shape defined by the gripping region when the rod is coupled in the gripping region such that a portion of the rod and the substantially circular shape defined by the gripping region extends outwardly from the top-most portion of the rod retaining member when the rod retaining member is in a fully engaged position; and an engaging tab on the fastener that couples the fastener to the rod retaining member to couple the rod retaining member to the tulip, the engaging tab being accessible through the side orifice of the tulip.

2. The pedicle screw and rod assembly of claim 1, further comprising:
an engagement tool including an outer housing configured to engage an outer wall of the tulip; and
at least one protrusion extending from an inner wall of the outer housing, the at least one protrusion being sized to enter the side orifice and release the engagement tab from interfering with the rod retaining member.

3. The pedicle screw and rod assembly of claim 1, wherein the fastener assembly is in direct contact with both the head portion of the screw and the rod retaining member.

4. A pedicle screw system comprising:
a screw having threads and a head;
a tulip coupled to the screw;
a fastener internal to the tulip and positioned to couple the tulip to the screw;
a rod retaining assembly that retains a rod, the rod retaining assembly having a substantial portion of the rod retaining assembly internal to the tulip; and an engaging tab on the fastener that couples the fastener to the rod retaining member to couple the rod retaining member to the tulip, the engaging tab being accessible through a side orifice of the tulip wherein the fastener is positioned between the rod retaining assembly and the screw; and
wherein the rod is retained within the rod retaining assembly such that a topmost portion of the rod extends above an outer top surface of said tulip, a top surface of the fastener, and a top surface of the rod retaining assembly when the rod retaining assembly is in a fully engaged position.

5. The pedicle screw system according to claim 4, wherein the top most portion of the rod retaining assembly is approximately at the same height as the top most portion of the tulip assembly.

6. The pedicle screw system according to claim 4, wherein the rod retaining assembly includes at least one split that permits the diameter of the rod retainer assembly to vary from a first, large diameter to a second, small diameter.

7. The pedicle screw system according to claim 4, wherein the fastener includes at least one split that permits the diameter of the fastener to vary from a first, large diameter to a second, small diameter.

8. The pedicle screw system of claim 4, wherein the rod retaining assembly defines a recess on a bottom surface thereof, at least a portion of the fastener being insertable into the recess.

\* \* \* \* \*